(12) United States Patent  
Pascal

(10) Patent No.: US 11,053,273 B2
(45) Date of Patent: *Jul. 6, 2021

(54) PROCESS FOR THE PRODUCTION OF ESTETROL INTERMEDIATES

(75) Inventor: Jean-Claude Pascal, Nice (FR)

(73) Assignee: ESTETRA S.P.R.L., Liege (BE)

( * ) Notice: Subject to any disclaimer, the term of this patent is extended or adjusted under 35 U.S.C. 154(b) by 210 days.

This patent is subject to a terminal disclaimer.

(21) Appl. No.: 14/122,892

(22) PCT Filed: Jun. 1, 2012

(86) PCT No.: PCT/EP2012/060446
§ 371 (c)(1),
(2), (4) Date: Nov. 27, 2013

(87) PCT Pub. No.: WO2012/164095
PCT Pub. Date: Dec. 6, 2012

(65) Prior Publication Data
US 2014/0107091 A1    Apr. 17, 2014

Related U.S. Application Data

(60) Provisional application No. 61/492,297, filed on Jun. 1, 2011.

(30) Foreign Application Priority Data

Jun. 1, 2011   (EP) .................................. 11168560.8

(51) Int. Cl.
| | | |
|---|---|---|
| *C07J 1/00* | (2006.01) | |
| *C07J 51/00* | (2006.01) | |
| *A61K 31/565* | (2006.01) | |

(52) U.S. Cl.
CPC ........... *C07J 1/0018* (2013.01); *A61K 31/565* (2013.01); *C07J 1/007* (2013.01); *C07J 1/0059* (2013.01); *C07J 51/00* (2013.01); *Y02P 20/55* (2015.11)

(58) Field of Classification Search
CPC ....... C07J 1/0018; A61K 31/565; Y02P 20/55
See application file for complete search history.

(56) References Cited

U.S. PATENT DOCUMENTS

| | | | |
|---|---|---|---|
| 3,138,588 A | 6/1964 | Smith | |
| 3,177,206 A | 4/1965 | Smith et al. | |
| (Continued) | | | |

FOREIGN PATENT DOCUMENTS

| | | | |
|---|---|---|---|
| CL | 2005-01207 A1 | 6/2006 | |
| CL | 2014-00802 A1 | 11/2014 | |
| (Continued) | | | |

OTHER PUBLICATIONS

Takeuchi et al., "Solvent Effecs and Steric Course in the Solvolysis of 1,3,3-Trimethyl-2-oxocyclopentyl Mesylate in Comparison with 1,1,3,3-Tetramethyl-2-oxobutyl System." Bull. Chem. Soc. Jpn., 74, pp. 363-370, 2001.*

(Continued)

*Primary Examiner* — Barbara P Badio
(74) *Attorney, Agent, or Firm* — Lathrop GPM LLP; James H. Velema, Esq.; Laura A. Labeots, Esq.

(57) ABSTRACT

The present invention relates to a process for the preparation of a compound of formula (I) comprising the steps of a) reacting a compound of formula (II) with a silylating or an acylating agent to produce compound of formula (III), wherein $P^1$ is a protecting group selected from $R^2$—Si—$R^3R^4$ or $R^1CO$—, $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl; b) halogenation or sulfinylation of the compound of formula (III) to produce a compound of formula (IV); wherein X is halo, or —O—SO—$R^5$, and $R^5$ is a group selected from $C_{6-10}$aryl or heteroaryl, each group being optionally substituted by one or more substituents independently selected from chloro or $C_{1-4}$alkyl; c) dehalogenation or desulfinylation of the compound of formula (IV) to produce compound of formula (V); and d) reacting the compound of formula (V) with a reducing agent to produce compound of formula (I).

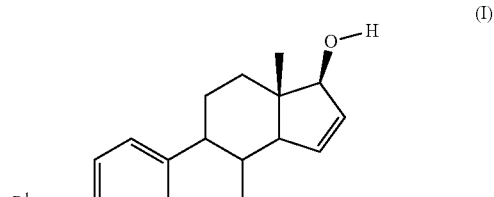

(I)

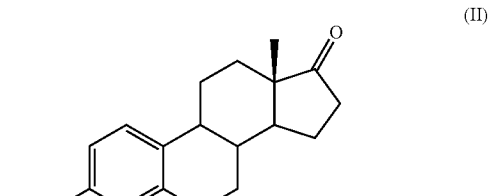

(II)

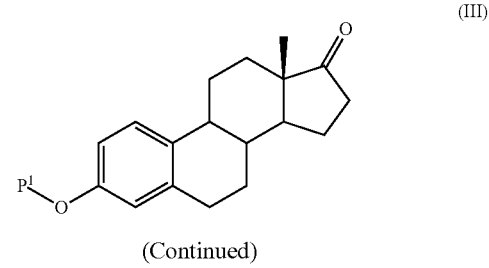

(III)

(Continued)

-continued

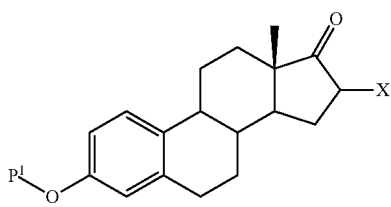
(IV)

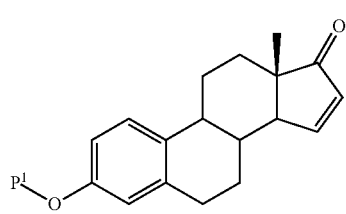

(V)

19 Claims, No Drawings

(56) References Cited

U.S. PATENT DOCUMENTS

| | | | |
|---|---|---|---|
| 3,433,785 | A | 3/1969 | Phillips et al. |
| 4,739,078 | A | 4/1988 | Perlman |
| 4,792,620 | A | 12/1988 | Paulik |
| 4,923,640 | A | 5/1990 | Bohlmann et al. |
| 5,340,586 | A | 8/1994 | Pike et al. |
| 6,117,446 | A | 9/2000 | Place |
| 6,541,465 | B2 * | 4/2003 | Loozen .............. C07J 1/0074 206/112 |
| 6,723,348 | B2 | 4/2004 | Faham et al. |
| 7,723,320 | B2 | 5/2010 | Bunschoten et al. |
| 7,732,430 | B2 | 6/2010 | Bunschoten et al. |
| 7,871,995 | B2 | 1/2011 | Bunschoten et al. |
| 7,923,440 | B2 | 4/2011 | Bunschoten et al. |
| 7,943,604 | B2 | 5/2011 | Coelingh Bennink et al. |
| 8,026,228 | B2 | 9/2011 | Coelingh Bennink et al. |
| 8,048,869 | B2 | 11/2011 | Bunschoten et al. |
| 8,236,785 | B2 | 8/2012 | Coelingh Bennink et al. |
| 8,367,647 | B2 | 2/2013 | Coelingh Bennink et al. |
| 8,518,923 | B2 | 8/2013 | Visser et al. |
| 8,987,240 | B2 | 3/2015 | Coelingh Bennink et al. |
| 8,987,484 | B2 | 3/2015 | Pascal et al. |
| 9,034,854 | B2 | 5/2015 | Coelingh Bennink et al. |
| 9,040,509 | B2 | 5/2015 | Coelingh Bennink et al. |
| 9,238,035 | B2 | 1/2016 | Foidart et al. |
| 9,561,238 | B2 | 2/2017 | Coelingh Bennink et al. |
| 9,579,329 | B2 | 2/2017 | Wouters |
| 9,603,860 | B2 | 3/2017 | Perrin et al. |
| 9,808,470 | B2 | 11/2017 | Foidart et al. |
| 9,884,064 | B2 | 2/2018 | Platteeuw et al. |
| 9,987,287 | B2 | 6/2018 | Platteeuw et al. |
| 9,988,417 | B2 | 6/2018 | Gil et al. |
| 2004/0192620 | A1 | 9/2004 | Bunschoten et al. |
| 2004/0198671 | A1 | 10/2004 | Bunschoten et al. |
| 2005/0032755 | A1 | 2/2005 | Van Look et al. |
| 2005/0070488 | A1 | 3/2005 | Coelingh Bennik et al. |
| 2005/0147670 | A1 | 7/2005 | Hsu et al. |
| 2006/0063723 | A1 | 3/2006 | Coelingh Bennink et al. |
| 2006/0211669 | A1 | 9/2006 | Verhaar et al. |
| 2006/0276414 | A1 | 12/2006 | Coelingh Bennink et al. |
| 2007/0048369 | A1 | 3/2007 | Foreman et al. |
| 2007/0286819 | A1 | 12/2007 | De Vries et al. |
| 2008/0113953 | A1 | 5/2008 | De Vries et al. |
| 2011/0250274 | A1 | 10/2011 | Shaked et al. |
| 2014/0107358 | A1 | 4/2014 | Pascal |
| 2014/0235882 | A1 | 8/2014 | Platteeuw et al. |
| 2015/0045300 | A1 | 2/2015 | Ahuja et al. |
| 2015/0105362 | A1 | 4/2015 | Verhaar et al. |
| 2015/0133413 | A1 | 5/2015 | Coelingh Bennink et al. |
| 2015/0182540 | A1 | 7/2015 | Heil et al. |
| 2016/0310506 | A1 | 10/2016 | Platteeuw et al. |
| 2016/0367567 | A1 | 12/2016 | Jaspart et al. |
| 2017/0196886 | A1 | 7/2017 | Wouters |
| 2017/0216318 | A1 | 8/2017 | Perrin et al. |
| 2017/0369521 | A1 | 12/2017 | Platteeuw et al. |
| 2018/0169022 | A1 | 6/2018 | Jaspart et al. |
| 2018/0185271 | A1 | 7/2018 | Jaspart et al. |
| 2018/0265540 | A1 | 9/2018 | Verhaar et al. |

FOREIGN PATENT DOCUMENTS

| | | |
|---|---|---|
| CN | 1197387 A | 10/1998 |
| CN | 101443015 A | 5/2009 |
| CN | 101541326 A | 9/2009 |
| CN | 101631536 A | 1/2010 |
| CN | 102058604 A | 5/2011 |
| DE | 21 29 943 A1 | 12/1971 |
| DE | 144 266 A1 | 10/1980 |
| EP | 0 277 676 A1 | 8/1988 |
| EP | 0371466 A1 | 6/1990 |
| EP | 0646592 A1 | 4/1995 |
| EP | 2077272 | 7/2009 |
| EP | 2077273 | 7/2009 |
| EP | 2077322 A2 | 7/2009 |
| EP | 2077812 A2 | 7/2009 |
| EP | 2085373 A1 | 8/2009 |
| EP | 2383279 A1 | 11/2011 |
| EP | 3046928 A1 | 7/2016 |
| EP | 3106148 A1 | 12/2016 |
| JP | S63-216895 A | 9/1988 |
| JP | 2005-523283 T | 8/2005 |
| JP | 2010-513514 T | 4/2010 |
| WO | WO 2000/042955 A1 | 7/2000 |
| WO | WO 01/05806 * | 1/2001 |
| WO | WO 2002/094275 A1 | 11/2002 |
| WO | WO 2002/094276 A1 | 11/2002 |
| WO | WO 2002/094278 A1 | 11/2002 |
| WO | WO 2002/094279 A1 | 11/2002 |
| WO | WO 2003/018026 A1 | 3/2003 |
| WO | WO 2003/041718 A1 | 5/2003 |
| WO | WO 2004/006936 A1 | 1/2004 |
| WO | 2004/041839 A2 | 5/2004 |
| WO | WO 2004/103377 A1 | 12/2004 |
| WO | 2006/125800 A1 | 11/2006 |
| WO | WO 2007/081206 A1 | 7/2007 |
| WO | WO 2008/156365 A1 | 6/2008 |
| WO | WO 2010/033832 A2 | 3/2010 |
| WO | WO 2010/089078 A1 | 8/2010 |
| WO | WO 2012/164095 A1 | 12/2012 |
| WO | WO 2013/012326 A1 | 1/2013 |
| WO | WO 2013/021025 A1 | 2/2013 |
| WO | WO 2014/159377 A1 | 10/2014 |
| WO | WO 2015/086643 A1 | 6/2015 |
| WO | WO 2016/203006 A1 | 12/2016 |
| WO | WO 2016/203009 A1 | 12/2016 |
| WO | WO 2016/203044 A1 | 12/2016 |

OTHER PUBLICATIONS

Green et al., "Compounds Related to the Seroid Hormones. Part II. The Action of Hydrogen Bromide on 2-Bromo-3-oxo-delta1-5alpha-Steroids." J. Chem. Soc., pp. 2532-2543, 1961.*

Heathcock et al., "Synthesis of Sesquiterpene Antitumor Lactones. 10. Total Synthesis of (+/−)-Parthenin." J. Am. Chem. Soc., 104, pp. 6081-6091, 1982.*

Wang et al., "Neurosteroid Analogues. Part 13: Synthetic Methods for the Preparation of 2beta-Hydroxygonane Derivatives as Structural Mimics of ent-3alpha-Hydroxysteroid Modulators of GABA-A Receptors." Tetrahedron, 63, pp. 7977-7984, 2007.*

Suzuki et al., "Synthesis of 15alpha-hydroxyestrogen 15-N-acetylglucosaminides.", Steroids, vol. 60, 277-284, 1995 (Year: 1995).*

Warmerdam et al. "A new route of synthesis of estetrol". Climacteric 2008, vol. 11, Suppl. 1, pp. 59-63.

(56) References Cited

OTHER PUBLICATIONS

Office Action in corresponding Chinese Patent Application No. 201280026131.6, dated Mar. 12, 2015.
Trost et al. 'Methyl 2-Pyridinesulfinate. A Convenient Reagent for Sulfinylation-Dehydrosulfinylation'. Journal of Organic Chemistry. 1993, vol. 58, No. 6, pp. 1579-1581.
International Preliminary Report on Patentability (PCT/EP2012/060446) (dated Dec. 2, 2013).
Written Opinion of the International Searching Authority (PCT/EP2012/060446), dated 2012.
International Application Published Under the Patent Cooperation Treaty (PCT/EP2012/060446) (Dec. 6, 2012).
Cantrall et al. (1964) "The Synthesis of C-15 β-Substituted Estra-1,3,5(10)-trienes. I," J. Org. Chem. 29(1):64-68.
Cantrall et al. (1964) "The Synthesis of C-15 β-Substituted Estra-1,3,5(10)-thenes. II," J. Org. Chem. 29(1):214-217.
Fishman et al. (1968) "Synthesis of epimeric 15-hydroxyestriols, new and potential metabolites of estradiol," J. Org. Chem. 33(8):3133-3135.
Johnson et al. (1957) "14-Isoestrone Methyl Ether and its Identity with Totally Synthetic Material," J. Am. Chem. Soc. 79:2005-2009.
Al-Jefout et al., "Continuous Norethisterone Acetate versus Cyclical Drospirenone 3 mg/Ethinyl Estradiol 20 ug for the Management of Primary Dysmenorrhea in Young Adult Women," Journal of Pediatric and Adolescent Gynecology, vol. 29, No. 2, pp. 143-147, XP029421056, 2011.
Andersch and Milsom: "An epidemiologic study of young women with dysmenorrhea", Am J Obstet Gynecol, 144(6), p. 655-660, 1982.
Anderson and Spencer: "Risk factors for venous thromboembolism", Circulation, 107, I-9-I-16, 2003.
Anderson et al., "Effects of conjugated equine estrogen in postmenopausal women with hysterectomy" The Women's Health Initiative randomized controlled trial, JAMA vol. 291(14), pp. 1701-1712, 2004.
Apter et al., "Bleeding pattern and cycle control with estetrol-containing combined oral contraceptives: results from a phase II, randomised, dose-finding study (FIESTA)", Contraception, 94(4), p. 366-373 (Oct. 2016), 2016.
Archer et al., "A randomized, double-blind, placebo-controlled study of the lowest effective dose of drospirenone with 17β-estradiol for moderate to severe vasomotor symptoms in postmenopausal women", Menopause, vol. 21(3), pp. 227-235, 2011.
Arnal et al., "Tissue specificity of the membrane vs nuclear actions of estrogen receptor alpha: insights from targeted mutations in mouse models," Archives of Cardiovascular Diseases Supplements, (Apr. 2016) vol. 8(3), p. 217, Abstract 0333, 2016.
Bagot et al., "The effect of estrone on thrombin generation may explain the different thrombotic risk between oral and transdermal hormone replacement therapy", J Thromb Haemost., 8(8):1736-1744, 2010.
Bennink et al. (2008) "Ovulation inhibition by estetrol in an in vivo model," Contraception. 77(3):186-190.
Bennink et al. (Apr. 2007) "Estetrol (E4), the forgotten fetal steroid," In; The Abstracts of the 9th European Congress of Endocrinology Meeting. Budapest, Hungary. vol. 14. Abstract No. S16.2.
Bennink et al., "Estetrol review: profile and potential clinical applications," Climacteric (2008) vol. 11, Suppl. 1, pp. 7-58, XP009194877.
Bennink et al., "Clinical effects of the fetal estrogen estetrol in a multiple-rising-dose study in postmenopausal women", Maturitas, Elsevier, Amsterdam, NL, vol. 91, 2016, pp. 93-100, XP029649879.
Bennink et al., "Pharmacokinetics of the fetal estrogen estetrol in a multiple-rising-dose study in postmenopausal women", Climacteric. 20(3), 2017, pp. 285-289.
Bennink et al., Pharmacodynamic effects of the fetal estrogen estetrol in postmenopausal women: results from a multiple-rising-dose study, Menopause 24(6), 2017, pp. 677-685.
Bianchi, "Estetrol: Desde un estrogeno fetal hasta el tratamiento de la menopausia", Rev Chil Obstet Ginecol, 74(2): 123-126, 2009.

Bjarnason et al.,"Acute and long-term estradiol kinetics in smoking postmenopausal women", Climacteric, vol. 15(5), pp. 449-454, 2012.
Bosworth et al., "Depressive symptoms, menopausal status, and climacteric symptoms in women at midlife", Psychosom Med., 63(4):603-8, 2001.
Bull et al. "Synthesis and structure-activity studies of 8a- and 9beta-analogues of 14, 17-ethanoestradiol"J. Chem. Soc., Perkin Trans. 1, 2000, pp. 1003-1013, 2000.
Cainelli G. et al Synthesis, pp. 45-47, 1989.
Callejo et al., "Effect of a low-dose oral contraceptive containing 20 microg ethinylestradiol and 150 microg desogestrel on dysmenorrhea", Contraception, 68(3), p. 183-188, 2003.
Chemical Land data sheet: LiAlH4 (lithium aluminum hydride), Mar. 12, 2011.
Chinese Office Action in corresponding Chinese Patent Application No. 2012/80026131.6, dated Mar. 12, 2015.
Dahlback et al., "Familial thrombophilia due to a previously unrecognized mechanism characterized by poor anticoagulant response to activated protein C: prediction of a cofactor to activated protein C", Proc Natl Acad Sci U S A., 90(3), p. 1004-1008, 1993.
Davis et al., "Oral contraceptives for dysmenorrhea in adolescent girls: a randomized trial", Obstet Gynaecol, 106(1): 97-104, 2005.
De Bastos et al., "Combined oral contraceptives: venous thrombosis", Cochrane Database Syst Rev, (3):CD010813, 2014.
Dinger et al., "Risk of venous thromboembolism and the use of dienogest- and drospirenone-containing oral contraceptives: results from a German case-control study", J Fam Plann Reprod Health Care, 36(3):123-129, 2010.
Dinger et al., *Effectiveness of Oral Contraceptive Pills in a Large U.S. Cohort Comparing Progestogen and Regimen*, Obstet. & Gynecol., 117(1):33-40 (2011).
Dinger et al., *Oral Contraceptive Effectiveness According to Body Mass Index, Weight, Age, and Other Factors*, Am. J. Obstet. Gynecol., 201:263e1-9 (2009).
Dionne P et al Steroids, vol. 62, pp. 674-681, 1997.
Dörwald, Side Reactions in Organic Synthesis, Wiley-VCH Verlag GmbH & Co. KGaA, Weinheim, Preface,. p. IX, 2005.
Duijkers et al., "Inhibition of ovulation by administration of estetrol in combination with drospirenone or levonorgestrel: Results of a phase II dose-finding pilot study", Eur J Contracept Reprod Health Care,.20(6), p. 476-489, 2015.
Duijkers et al., "A randomized study comparing the effect on Ovarian activity of a progestogen-only pill (POP) containing desogestrel and a new POP containing drospirenone in a 24/4 regimen", Euro. J. Contracept. & Repro. Health Care, 20(6):419-27 (2015).
Egner et al. (1999) "7a,15a-Ethano bridged steroids. Synthesis and progesterone receptor interaction," Tetrahedron. 55:11267-11274.
Elger et al., "Conception and pharmacodynamics profile of drospirenone", Steriods, 68(10):891-905 (2003).
Endrikat et al., "A twelve-month comparative clinical investigation of two low-dose oral contraceptives containing 20 micrograms ethinylestradiol/75 micrograms gestodene and 20 micrograms ethinylestradiol/150 micrograms desogestrel, with respect to efficacy, cycle control and tolerance", Contraception, 52(4), p. 229-235, 1995.
Erkkola et al. (2005) "Role of progestins in contraception," Acta Obstet. Gynecol. Scand. 84(3):207-216.
Fine (2011) "Update on emergency contraception," Adv. Ther. 28(2):87-90.
Foidart, "Estetrol, the first human, physiological Selective Estrogen Receptor Modulator," Presented at Eur. Soc. Contraception & Reprod. Health, 14th Cong, 2nd Global Conf., 2016.
French "Dysmenorrhea", Am Fam Physician, 71(2): 285-291, 2005.
Gardouh et al., "Preparation and characterization of mucoadhesive buccal film for delivery of meloxicam", British J. of Pharmaceutical Research, 3(4): 743-766, 2013.
Greene Protective Groups in Organic Chemistry, John Wiley & Sons, New York, pp. 44-46 and 53-55, 1999.
Greene, Theodora W. et al. Protective Groups in Organic Synthesis, 3rd edition, pp. 113-179, 1999.

(56) References Cited

OTHER PUBLICATIONS

Haque et al., "Development of polymer-bound fast-dissolving metformin buccal film with disintegrants", Int. J. of Nanomedicine, 10: 199-205, 2015.
Harel., "Dysmenorrhea in adolescents and young adults: an update on pharmacological treatments and management strategies," Expert Opinion on Pharmacotherapy, vol. 13 No. 15, pp. 2157-2170, XP055389783, 2012.
Harlow et al., "Executive summary of the Stages of Reproductive Aging Workshop + 10: addressing the unfinished agenda of staging reproductive aging", Menopause, vol. 19(4), 2012.
Harrington et al., "Cross-sectional association of endogenous steroid hormone, sex hormone-binding globulin, and precursor steroid levels with hemostatic factor levels in postmenopausal women", J Thromb Haemost., 15(1), p. 80-90, 2017.
Heinemann et al., International versions of the Menopause Rating Scale (MRS), Health Qual Life Outcomes, pp. 1:28, 2003.
Heinemann et al., The Menopause Rating Scale (MRS) as outcome measure for hormone treatment? A validation study, Health Qual Life Outcomes, pp. 2:67, 2004.
Heinemann et al., "The Menopause Rating Scale (MRS) scale: A methodological review", Health Qual Life Outcomes, pp. 2:45, 2004.
Hendrix and Alexander: "Primary dysmenorrhea treatment with a desogestrel-containing low-dose oral contraceptive", 66(6), p. 393-399, 2002.
Hilditch et al., "A menopause specific quality of life questionnaire: development and psychometric properties", Maturitas, vol. 24(3), pp. 161-175, 1996.
International Preliminary Report on Patentability, PCT/EP2012/060447, dated Oct. 16, 2013, 9 pages.
International Preliminary Report on Patentability, PCT/EP2012/060446, dated Dec. 2, 2013, 6 pages.
International Search Report and Written Opinion for PCT International Patent Application No. PCT/EP2012/060446, dated Dec. 6, 2012, 8 pages.
International Search Report with Written Opinion corresponding to International Patent Application No. PCT/EP2012/065572, dated Nov. 15, 2012, 8 pages.
Jick et al., "Risk of idiopathic cardiovascular death and nonfatal venous thromboembolism in women using oral contraceptives with differing progestagen components", Lancet, 346(8990): p. 1589-1593, 1995.
Johnson, William S. and Johns, William F., "14-Isoestrone Methyl Ether and its Identity with Totally Synthetic Material", J. Am. Chem. Soc., vol. 79, pp. 2005-2009.
Kluft et al: "Reduced hemostatic effects with drospirenone-based oral contraceptives containing estetrol vs ethinyl estradiol", Contraception, vol. 95, No. 2, p. 140-147, 2017.
Larock et al., "A Simple, Effective, New, Palladium-Catalyzed Conversion of Enol Silanes to Enones and Enals." Tetrahedron Letters. 1995, 36(14):2423-2426.
Li et al., "Stereoselective synthesis of some methyl-substituted steroid hormones and their in vitro cytotoxic activity against human gastric cancer cell line MGC-803", Steroids; 2010, vol. 75, No. 12, pp. 859-869.
Lidegaard et al., "Hormonal contraception and risk of venous trhomboembolism: national follow-study", BMJ, 339:b2890, 2009.
Lidegaard et al., "Risk of venous thromboembolism from use of oral contraceptives containing different progestogens and oestrogen doses: Danish cohort study, 2001-9", BMJ, 343:d6423, 2011.
Liu et al, "5-(Trimethylstannyl)-2H-pyran-2-one and 3-(Trimethylstannyl)-2H-pyran-2-one: New 2H-Pyran-2-one Synthons", J Org Chem; 1996, vol. 61, No. 19, pp. 6693-6699.
Luo Lianmei et al., Major research advances in estetrol, J Reprod Med, vol. 18(3), pp. 305-308, 2009.
Magnus P et al J. Am. Chem. Soc., vol. 120, pp. 12486-12499, 1998.
Matsui M. et al. J. Chem. Soc., Perkin Trans. I, pp. 1429-1432, 2005.
Mawet et al., "Unique effects on hepatic function, lipid metabolism, bone and growth endocrine parameters of estetrol in combined oral contraceptives", Eur J Contracept Reprod Health Care, 20(6), p. 463-475, 2015.
Minami et al. (1964)"New synthetic methods for $\alpha,\beta$-unsaturatedketones, aldehydes, esters and lactones by the palladium-catalyzed reactions of silyl enol eithers, ketene silyl acetals, and enol acetates with allyl carbonates," Tetrahedron. 42:2971-2977.
Mueller, George P et al. The Journal of Organic Chemistry, 26 (7), pp. 2403-2413.
Nambara T et al "Synthesis of Estetrol Monoglucuronides", Steroids, vol. 27, No. 1, pp. 111-122, XP009004815, 1976.
Nicolaou K.C. et al. Angewandte Chemie, vol. 41, No. 6, pp. 996-1000, XP002659963, 2002.
Norskov et al Nature Chemistry, 2009, 1, pp. 37-46, 2009.
Notelovitz et al., Initial 17$\beta$-Estradiol Dose for Treating Vasomotor Symptoms, Obstetrics and Gynaecology, vol. 95(5), pp. 726-731, 2000.
Odlind et al., "Can changes in sex hormone binding globulin predict the risk of venous thromboembolism with combined oral contraceptive pills?", Acta Obstet. Gynecol. Scand., 81(6), p. 482-490, 2002.
Ozanne et al. Organic Letters, vol. 5, No. 16, pp. 2903-2906, 2003.
Poirier D et al "Synthesis of 17beta-estradiol derivatives with N-Butyl, N-Methyl Alkylamide Side Chain at Position 15", Tetrahedron, vol. 47, No. 37, pp. 7751-7766, XP001122350, 1991.
Poort et al., "A common genetic variation in the 3'-untranslated region of the prothrombin gene is associated with elevated plasma prothrombin levels and an increase in venous thrombosis", Blood, 88(10), p. 3698-3703, 1996.
Portman et al., Genitourinary syndrome of menopause: new terminology for vulvovaginal atrophy from the International Society for the Study of Women's Sexual Health and the North American Menopause Society, Menopause, vol. 21(10), pp. 1063-1068, 2014.
Proctor and Farquhar: "Dysmenorrhoea", Clin Evid, 9, p. 1994-2013, 2007.
Reactivity Chart 1: Protection for Hydroxyl Group: Ethers, Greene's Protective Groups in Organic Synthesis, 3E, pp. 708-711, 1999.
Rodstrom et al., "A longitudinal study of the treatment of 25 hot flushes: the population study of women in Gothenburg during a quarter of a century", Menopause, vol. 9(3), pp. 156-161, 2002.
Rosenbaum et al., "Inhibition of ovulation by a novel progestogen (drospirenone) alone or in combination with ethinylestradiol", Euro. J. Contracept. & Repro. Health Care, 5(1):14-24 (2000).
Rosing et al., "Oral contraceptives and venous thrombosis: different sensitivities to activated protein C in women using second- and third-generation oral contraceptives", Br J Haematol., 97(1), p. 233-238, 1997.
Sakakibara M. et al Biosci. Biotech. Biochem., vol. 60, pp. 411-414, 1996.
Santoro, Symptoms of menopause: hot flushes, Clin Obstet Gynecol, vol. 51(3), pp. 539-548, 2008.
Savjani et al., "Drug solubility: importance and enhancement techniques", ISRN Pharm., 2012: 195727.
Sidney et al., "Recent combined hormonal contraceptives (CHCs) and the risk of thromboembolism and other cardiovascular events in new users", Contraception, 87(1), pp. 93-100, 2013.
Simon et al., "Menopausal hormone therapy for vasomotor symptoms: balancing the risks and benefits with ultra-low doses of estrogen", Expert Opin Investig Drugs, vol. 16(12), pp. 2005-2020, 2007.
Simoni et al., "The Discovery of Estrone, Estriol, and Estradiol and the Biochemical Study of Reproduction", The Work of Edward Adelbert Doisy, J. Biol. Chem., vol. 277, No. 28 e17, 2002.
Smith III et al. J. Org. Chem., vol. 72, pp. 4611-4620, 2007.
Smith III et al. Organic Letters, vol. 8, No. 10, pp. 2167-2170, 2006.
Spitzer et al., "Third generation oral contraceptives and risk of venous thromboembolic disorders: an international case-control study. Transnational Research Group on Oral Contraceptives and the Health of Young Women", BMJ, 312(7023), p. 83-88, 1996.
Strowitzki et al., "Efficacy of ethinylestradiol 20 µg/drospirenone 3 mg in a flexible extended reimen in women with moderate-to-severe

(56) References Cited

OTHER PUBLICATIONS primlary dysmenorrhea: an open-label, multicenter, ramdomised, controlled study," J. Fam. Plann. Reprod. Health Care (2012) vol. 38, pp. 94-101, 2012.

Sundell et al., "Factors influencing the prevalence and severity of dysmenorrhoea in young women.", Br J Obstet Gynaecol, 97(7), p. 588-594, 1990.

Takahashi et al. (1984) "Palladium-catalyzed chirality transfer of 1,3-diene monoepoxides and its application to the synthesis of steroid side chains," Tetrahedron Letters. 25:1921-1924.

Takahashi et al. (1985) "Regio- and stereoselective introduction of 156-hydroxy group and side chains to steroids by the palladium-catalyzed reaction of 1,3-diene monoepoxide," Tetrahedron. 41:5747-5754.

Tchaicovski and Rosing: "Mechanisms of estrogen-induced venous thromboembolism", Thromb Res., 126(1):5-11, 2010.

Utian et al., "Comparative controlled trial of a novel oral estrogen therapy, estradiol acetate, for relief of menopause symptoms", Menopause, vol. 12(6), pp. 708-715, 2005.

Visser et al. (2009) "Clinical applications for estetrol," J. Steroid. Biochem. Mol. Biol. 114(1-2):85-89.

Vlieg et al: "The venous thrombotic risk of oral contraceptives, effects of oestrogen dose and progestogen type: results of the MEGA case-control study", BMJ, 339:b2921, 2009.

Williams et al., "Strategies to address low drug solubility in discovery and development", Pharmacological Reviews, vol. 65(1), pp. 416-445, 2013.

Winkler et al., "Cycle control, quality of life and acne with two low-dose oral contraceptives containing 20 microg ethinylestradiol", Contraception, 96(6), p. 469-476, 2004.

Wong et al., "Oral contraceptive pill as treatment for pirmary dysmenorrhoea", Cochrane Database Syst Rev., CD002120, 2001.

Wto, "Venous thromboembolic disease and combined oral contraceptives: results of international multicentre case-control study", Lancet, 346(8990): p. 1575-1582, 1995.

Yamada et al., Specialty Chemicals Magazine, Catalysts, pp. 18-20.

Ylikorkala and Dawood, "New concepts in dysmenorrhea", Am J Obstet Gynecol, 130(7), p. 833-847, 1978.

Zhang and Wan Po, Efficacy of minor analgesics in primary dysmenorrhoea: a systematic review, 1998.

\* cited by examiner

PROCESS FOR THE PRODUCTION OF ESTETROL INTERMEDIATES

RELATED APPLICATIONS

This application is a 35 U.S.C. § 371 filing of International Application No. PCT/EP2012/060446, filed Jun. 1, 2012; which claims priority to European Patent Application No. 11168560.8, filed on Jun. 1, 2011 and U.S. Provisional Patent Application No. 61/492,297, filed on Jun. 1, 2011. The entire contents of each are incorporated herein by reference.

FIELD OF THE INVENTION

The present invention relates to a new process for the synthesis of a key intermediate in the synthesis of estetrol.

BACKGROUND OF THE INVENTION

Estrogenic substances are commonly used in methods of Hormone Replacement Therapy (HRT) and methods of female contraception. Estetrol is a biogenic estrogen that is endogenously produced by the fetal liver during human pregnancy. Recently, estetrol has been found effective as an estrogenic substance for use in HRT. Other important applications of estetrol are in the fields of contraception, therapy of auto-immune diseases, prevention and therapy of breast and colon tumors, enhancement of libido, skin care, and wound healing.

The synthesis of estetrol and derivatives thereof is known in the art. Verhaar M. T; et al (WO 2004/041839) describes a process for the preparation of estetrol starting from a 3-A-oxy-estra 1,3,5(10),15-tetraen-17-one, wherein A is a $C_1$-$C_5$ alkyl group, or a $C_7$-$C_{12}$ benzylic group. In this document, 3-A-oxy-estra 1,3,5(10),15-tetraen-17-ol is prepared in 6 steps from estrone where A is a benzyl group, the steps comprising protection of the 3-OH group by a benzyl group, then transformation of the 17-keto-group to a 17,17-ethylenedioxy derivative which is halogenated at the $C_{16}$ position using pyridinium bromide perbromide. Dehydrohalogenation is carried out by using potassium terbutoxyde in dimethylsulfoxide. Deprotection of the 17-keto-group is conducted using p-toluene-sulfonic acid monohydrate in aqueous acetone. Reduction of 17-keto-group affords the 17-ol derivative.

One of the disadvantages of the process described in WO 2004/041839 is the protection of 3-OH function with a benzyl group which can be removed only by hydrogenation using Pd/C as catalyst in the last steps of the estetrol synthesis. Furthermore the level of this catalyst in the final drug substance must be determined and must comply with the ICH guidelines.

Another disadvantage of the synthesis described in WO 2004/041839 is the two step protection/deprotection of the 17-keto function in order to generate the 15-16 double bond with a low yield.

There remain a need for an improved synthesis of 3-Protected-oxy-estra-1,3,5(10),15-tetraene-17-ol. It is therefore an object of the present invention to provide a process for the preparation of 3-Protected-oxy-estra-1,3,5(10),15-tetraene-17-ol which overcome at least one the disadvantages of the prior art.

SUMMARY OF THE INVENTION

The present inventors have now found that this object can be obtained by using a process as defined in the appended claims.

According to a first aspect of the present invention, a process for the preparation of a compound of formula (I) (3-$P^1$-oxy-estra-1,3,5(10),15-tetraene-17-ol) is provided:

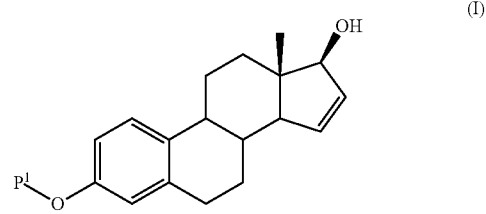

said process comprises the steps of a) reacting a compound of formula (II) with a silylating or an acylating agent to produce compound of formula (II), wherein $P^1$ is a protecting group selected from $R^2$—Si—$R^3R^4$ or $R^1CO$—, $R^1$ is a group selected from $C_{1-6}$alkyl or $C_{3-6}$cycloalkyl, each group being optionally substituted by one or more substituents independently selected from fluoro or $C_{1-4}$alkyl; $R^2$, $R^3$ and $R^4$ are each independently a group selected from $C_{1-6}$alkyl or phenyl, each group being optionally substituted by one or more substituents independently selected from fluoro or $C_{1-4}$alkyl;

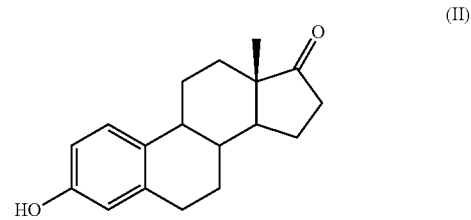

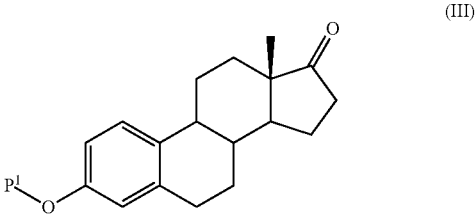

b) halogenation or sulfinylation of the compound of formula (II) to produce a compound of formula (IV); wherein X is halo, or —O—SO—$R^5$, and $R^5$ is a group selected from $C_{6-10}$aryl or heteroaryl, each group being optionally substituted by one or more substituents independently selected from chloro or $C_{1-4}$alkyl;

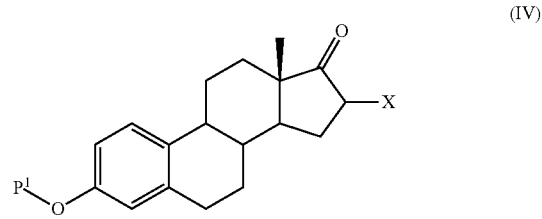

c) dehalogenation or desulfinylation of the compound of formula (IV) to produce compound of formula (V); and

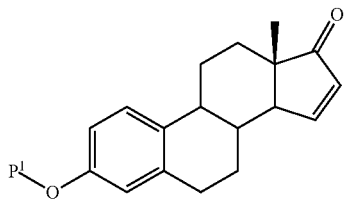

(V)

d) reacting the compound of formula (V) with a reducing agent to produce compound of formula (I).

The invention provides an improved process for producing 3-P$^1$-oxy-estra-1,3,5(10),15-tetraene-17-ol of formula (I) in significantly higher yield and for at lower cost than possible by the previous known syntheses.

According to a second aspect, the present invention also encompasses a process for the preparation of estetrol, said process comprising preparing a compound of formula (I) by a process according to the first aspect of the invention and further reacting the compound of formula (I) to produce estetrol.

According to a third aspect, the present invention also encompasses estetrol directly obtained by the process according to the second aspect of the invention, for use in a method selected from a method of hormone replacement therapy, a method of treating vaginal dryness, a method of contraception, a method of enhancing libido, of method of treating skin, a method of promoting wound healing, and a method of treating or preventing a disorder selected from the group consisting of autoimmune diseases, breast tumors and colorectal tumors.

The above and other characteristics, features and advantages of the present invention will become apparent from the following detailed description, which illustrate, by way of example, the principles of the invention.

DETAILED DESCRIPTION OF THE INVENTION

It is to be understood that the terminology used herein is not intended to be limiting, since the scope of the present invention will be limited only by the appended claims.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. It will be appreciated that the terms "comprising", "comprises" and "comprised of" as used herein comprise the terms "consisting of", "consists" and "consists of".

The recitation of numerical ranges by endpoints includes all numbers and fractions subsumed within the respective ranges, as well as the recited endpoints.

All references cited in the present specification are hereby incorporated by reference in their entirety. In particular, the teachings of all references herein specifically referred to are incorporated by reference.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

The term "alkyl" by itself or as part of another substituent, refers to a straight or branched saturated hydrocarbon group joined by single carbon-carbon bonds having 1 to 6 carbon atoms, for example 1 to 5 carbon atoms, for example 1 to 4 carbon atoms, preferably 1 to 3 carbon atoms. When a subscript is used herein following a carbon atom, the subscript refers to the number of carbon atoms that the named group may contain. Thus, for example, $C_{1-6}$alkyl means an alkyl of one to six carbon atoms. Examples of alkyl groups are methyl, ethyl, propyl, isopropyl, butyl, isobutyl, sec-butyl, tert-butyl, 2-methylbutyl, pentyl iso-amyl and its isomers, hexyl and its isomers.

The term "$C_{3-6}$cycloalkyl", as a group or part of a group, refers to a saturated cyclic alkyl radical containing from about 3 to about 6 carbon atoms. Examples of monocyclic $C_{3-6}$cycloalkyl radicals include cyclopropyl, cyclobutyl, cyclopentyl, or cyclohexyl.

The term "$C_{2-6}$alkenyl" by itself or as part of another substituent, refers to an unsaturated hydrocarbyl group, which may be linear, or branched, comprising one or more carbon-carbon double bonds. Examples of $C_{2-6}$alkenyl groups are ethenyl, 2-propenyl, 2-butenyl, 3-butenyl, 2-pentenyl and its isomers, 2-hexenyl and its isomers, 2,4-pentadienyl and the like.

The term "$C_{6-10}$aryl", by itself or as part of another substituent, refers to a polyunsaturated, aromatic hydrocarbyl group having a single ring (i.e. phenyl) or multiple aromatic rings fused together (e.g. naphthyl). or linked covalently, typically containing from 6 to 10 carbon atoms, wherein at least one ring is aromatic. $C_{6-10}$aryl is also intended to include the partially hydrogenated derivatives of the carbocyclic systems enumerated herein. Non-limiting examples of $C_{6-10}$aryl comprise phenyl, naphthyl, indanyl, or 1,2,3,4-tetrahydro-naphthyl.

The term "halo" or "halogen" as a group or part of a group is generic for fluoro, chloro, bromo, or iodo.

The term "$C_{6-10}arylC_{1-6}alkyl$", by itself or as part of another substituent, refers to a $C_{1-6}alkyl$ group as defined herein, wherein one or more hydrogen atoms are replaced by one or more $C_{6-10}aryl$ as defined herein. Examples of aralkyl radicals include benzyl, phenethyl, dibenzylmethyl, methylphenylmethyl, 3-(2-naphthyl)-butyl, and the like.

The term "$C_{1-6}alkylcarbonyl$", as a group or part of a group, represents a group of Formula —CO—$R^a$, wherein $R^a$ is $C_{1-6}alkyl$ as defined herein.

The term "$C_{3-6}cycloalkylcarbonyl$", as a group or part of a group, represents a group of Formula —CO—$R^c$, wherein $R^a$ is $C_{3-6}cycloalkyl$ as defined herein.

The term "$C_{2-6}alkenylC_{1-6}alkanoate$" refers to a compound having the Formula $R^b$—O—CO—$R^a$ wherein $R^a$ is $C_{1-6}alkyl$ as defined herein and $R^b$ is $C_{2-6}alkenyl$ as defined herein.

The term "$C_{2-6}alkenylC_{3-6}cycloalkanoate$" refers to a compound having the Formula $R^b$—O—CO—$R^c$ wherein $R^c$ is $C_{3-6}cycloalkyl$ as defined herein and $R^b$ is $C_{2-6}alkenyl$ as defined herein.

The term "heteroaryl", by itself or as part of another substituent, refers to an aromatic monocyclic or polycyclic heterocycles having preferably 5 to 7 ring atoms and more preferably 5 to 6 ring atoms, which contains one or more heteroatom ring members selected from nitrogen, oxygen or sulfur. Non-limiting examples of a heteroaryl include: pyridinyl, pyrrolyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, pyridazinyl, oxazinyl, dioxinyl, thiazinyl, triazinyl. Preferably heteroaryl is selected from the group comprising pyridinyl, pyrrolyl, furanyl, thiophenyl, imidazolyl, pyrazolyl, oxazolyl, thiazolyl, and pyrazinyl. More preferably heteroaryl is pyridinyl.

The present invention relates to a process for preparing 3-$P^1$-oxy-estra-1,3,5(10),15-tetraene-17-ol of formula (I), wherein $P^1$ is a protecting group selected from $R^2$—Si—$R^3R^4$; or $R^1CO$—, wherein $R^1$ is a group selected from $C_{1-6}alkyl$ or $C_{3-6}cycloalkyl$, each group being optionally substituted by 1, 2 or 3 substituents independently selected from fluoro or $C_{1-4}alkyl$; preferably $R^1$ is selected from the group comprising methyl, ethyl, propyl, isopropyl, butyl, isobutyl, tert-butyl, cyclopropyl, cyclobutyl, cyclopentyl, or cyclohexyl, each group being optionally substituted by 1, 2 or 3 substituents independently selected from fluoro or $C_{1-4}alkyl$; more preferably $R^1$ is methyl, ethyl, propyl, isopropyl, cyclopentyl, or cyclohexyl, yet more preferably $R^1$ is methyl, or ethyl;

$R^2$, $R^3$ and $R^4$ are each independently a group selected from $C_{1-6}alkyl$ or phenyl, said $C_{1-6}alkyl$ or phenyl, being optionally substituted with 1, 2 or 3 substituents independently selected from fluoro or $C_{1-6}alkyl$; preferably $R^2$, $R^3$ and $R^4$ are each independently selected from the group comprising methyl, ethyl, propyl, isopropyl, butyl, isobutyl, tert-butyl, and phenyl, each group being optionally substituted with 1, 2 or 3 substituents each independently selected from fluoro or $C_{1-4}alkyl$; preferably $R^2$, $R^3$ and $R^4$ are each independently selected from the group comprising methyl, ethyl, propyl, isopropyl, or tert-butyl, and phenyl, each group being optionally substituted with 1, 2 or 3 substituents each independently selected from fluoro or $C_{1-2}alkyl$,

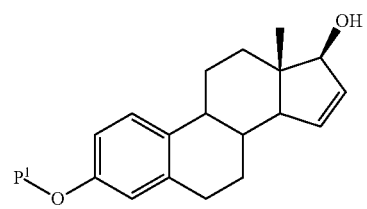

said process comprising the steps of:

a) protecting the hydroxyl of estrone of formula (II) to produce compound of formula (III), wherein $P^1$ is as defined above, b) halogenation or sulfinylation of the compound of formula (II) to produce a compound of formula (IV); wherein X is halo, or —O—SO—$R^5$, and $R^5$ is a group selected from $C_{6-10}aryl$ or heteroaryl, each group being optionally substituted by one or more substituents independently selected from chloro or $C_{1-4}alkyl$;

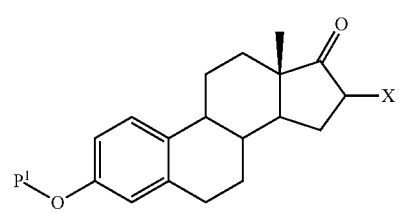

c) dehalogenation or desulfinylation of the compound of formula (IV) to produce compound of formula (V); and

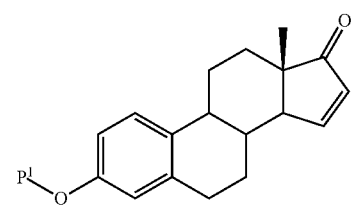

d) reacting the compound of formula (V) with a reducing agent to produce compound of formula (I);
and if necessary any protective group used in the reactions described above is cleaved concurrently or subsequently; and
if desired, compound of formula (I) is subsequently converted into another compound by routine processes applicable for conversion of functional groups,
if desired a compound of formula I thus obtained is resolved into its stereoisomers.

In an embodiment, $P^1$ is $R^2$—Si—$R^3R^4$. Preferably $P^1$ is selected from the group comprising tert-butyl-dimethyl-silyl, diphenyl-methyl-silyl, dimethyl-phenyl-silyl, trimethyl-silyl, triethyl-silyl and triisopropyl-silyl, each group being optionally substituted by one or more substituents independently selected from fluoro or $C_{1-4}alkyl$; more preferably $P^1$ is tert-butyl-dimethyl-silyl.

In an embodiment, the silylating agent can be selected from the group comprising $C_{1-6}alkylsilylchloride$, $C_{1-6}alkylsilyltriflate$, phenylsilylchloride, phenylsilyltriflate, $C_{1-6}$alkyl phenylsilylchloride, $C_{1-6}$alkylphenylsilyltriflate, each group being optionally substituted by one or more substituents independently selected from fluoro or $C_{1-4}$alkyl.

In another embodiment, $P^1$ is $R^1CO$—; preferably $P^1$ is a group selected from $C_{1-4}$alkylcarbonyl or $C_{4-6}$cycloalkylcarbonyl, each group being optionally substituted by 1, 2 or 3 substituents independently selected from fluoro or $C_{1-4}$alkyl; more preferably $P^1$ is a group selected from $C_{1-2}$alkylcarbonyl or $C_{5-6}$cycloalkylcarbonyl, each group being optionally substituted by 1, 2 or 3 substituents independently selected from fluoro or $C_{1-2}$alkyl; for example $P^1$ is selected from acetyl, or cyclohexylcarbonyl, preferably $P^1$ is acetyl.

In an embodiment, the process for the preparation of 3-$P^1$-estra 1,3,5(10),15-tetraene-17-ol of formula (I) from estrone of formula (II) can be preformed as shown in Scheme 1. The compound of formula (I) can then be further reacted to prepare estetrol.

ride, dimethylphenylsilylchloride, trimethylsilylchloride, triethylsilylchloride, or triisopropylsilylchloride, or such as tert-butyl dimethylsilyltriflate, diphenylmethylsilyltriflate, dimethylphenylsilyltriflate, trimethylsilyltriflate, triethylsilyltriflate, or triisopropylsilyltriflate. The reaction can be performed in the presence of a suitable base such as imidazole, 2,6-lutidine, collidine, triethylamine, or 1,8-diazabicyclo[5.4.0]undec-7-ene (DBU). The reaction can be performed at room temperature or under reflux. The reaction can be performed in the presence of a suitable solvent such as dichloromethane, toluene, or dimethylformamide or a mixture thereof.

In another embodiment, estrone of formula (II) is reacted with an acylating agent. In an embodiment, said acylating agent can be selected from the group comprising $C_{2-6}$alkenyl$C_{1-6}$alkanoate, $C_{2-6}$alkenyl$C_{3-6}$cycloalkanoate, acyl chloride, and anhydrides. Preferably, the acylating agent is Scheme 1

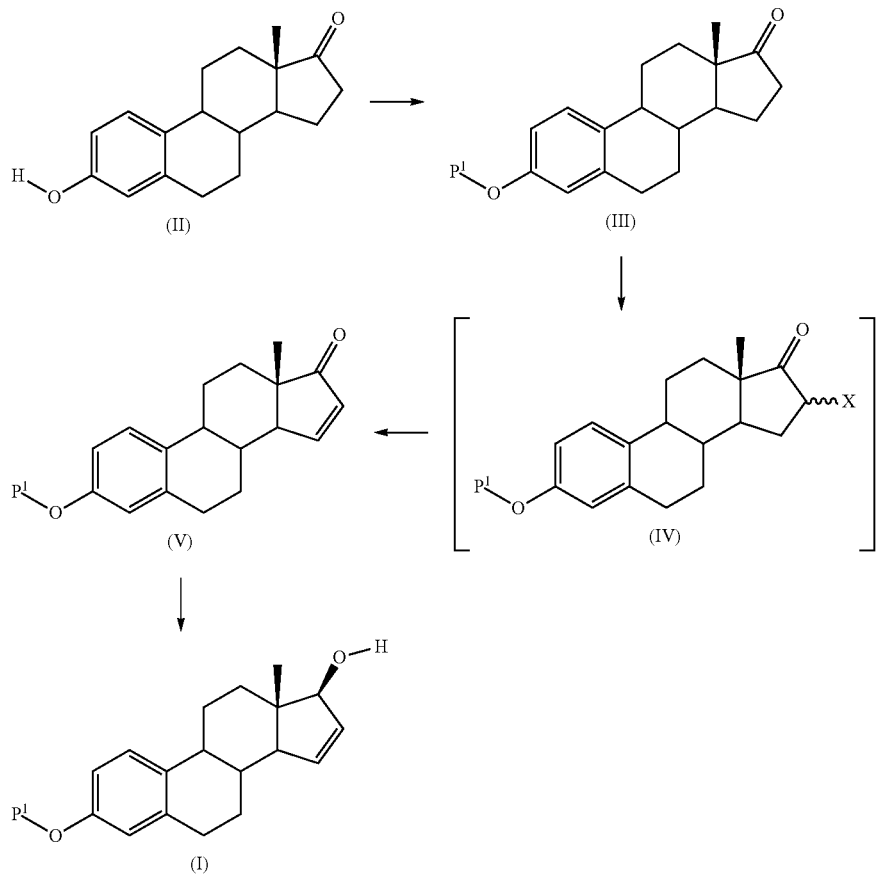

According to scheme 1, the hydroxyl of estrone of formula (II) is protected, to produce compound of formula (III).

In an embodiment, estrone of formula (II) is reacted with a silylating agent. The silylating agent can be selected from the group comprising $C_{1-6}$alkylsilylchloride, $C_{1-6}$alkylsilyltriflate, phenylsilylchloride, phenylsilyltriflate, $C_{1-6}$alkylphenylsilyl chloride, $C_{1-6}$alkylphenylsilyltriflate, each group being optionally substituted by one or more substituents independently selected from fluoro or $C_{1-4}$alkyl.

For example, formation of protected estrone silyl ether can be performed by reaction of a silylating agent such as tert-butyl dimethylsilylchloride, diphenylmethylsilylchloselected from the group comprising $C_{2-6}$alkenylpropanoate, $C_{2-6}$alkenylbutanoate, $C_{2-6}$alkenylpentanoate, $C_{2-6}$alkenylhexanoate, $C_{2-6}$alkenylcyclopropanoate, $C_{2-6}$alkenylcyclobutanoate, $C_{2-6}$alkenylcyclopentanoate, and $C_{2-6}$alkenylcyclohexanoate, acyl chloride and anhydrides. More preferably, the acylating agent is selected from the group comprising isopropenyl acetate, isopropenyl propionate, isopropenyl butyrate, isopropenyl isobutyrate, vinyl acetate, vinyl propionate, prop-2-enyl cyclohexanecarboxylate, ethenyl cyclopentanecarboxylate, vinyl cyclohexanoate, acetyl chloride, propionylchloride, butyrylchloride, acetic anhydride and the like. More preferably, the acylating agent is selected from the group comprising isopropenyl acetate, isopropenyl propionate, isopropenyl butyrate, isopropenyl isobutyrate, vinyl acetate, vinyl propionate, acetyl chloride, propionylchloride, butyrylchloride, acetic anhydride and the like.

The acylation when performed with $C_{2-6}$alkenyl$C_{1-6}$alkanoate or $C_{2-6}$alkenyl$C_{3-6}$cycloalkanoate, can be performed in the presence of an acid, such as in the presence of sulfuric acid, or in the presence of a $C_{6-10}$arylsulfonic acid, optionally substituted by one or more chloro substituents. Non-limiting examples of a suitable acid include paratoluene sulfonic acid, and sulfuric acid.

The acylation when performed with an acyl chloride or an anhydride, can be performed in the presence of an organic base, such as imidazole, triethylamine and the like.

Step (b) of the process comprises halogenation or sulfinylation of the compound of formula (III) to produce a compound of formula (IV); wherein X is halo, or —O—SO—$R^5$, and $R^5$ is a group selected from $C_{6-10}$aryl or heteroaryl, each group being optionally substituted by one or more substituents independently selected from chloro or $C_{1-4}$alkyl; preferably $R^5$ is phenyl or pyridinyl.

In an embodiment, step (b) is a halogenation and the halogenation is performed by reacting the compound of formula (III) with a halogenating reagent.

Preferably, step b) is a bromination, and X is bromo. In an embodiment, the brominating reagent can be selected from the group comprising copper(II) bromide, bromine, pyridine bromine perbromine and the like.

In another embodiment, step (b) is a sulfinylation and the sulfinylation is performed by reacting the compound of formula (III) with a base and with a sulfinylation reagent.

Non-limiting examples of sulfinylation reagent include methyl 2-pyridinesulfinate, methyl benzenesulfinate, methyl 4-methyl-benzenesulfinate, and methyl 4-chloro-benzene sulfinate.

The base used in the sulfinylation step can be selected from the group comprising potassium hydride, potassium terbutylate, sodium hydride, sodium terbutylate and a mixture thereof.

Non-limiting examples of suitable experimental conditions for the sulfinylation are described in Barry M Trost et al in Journal of Organic Chemistry, 1993, 58, 1579-81; hereby incorporated by reference.

The next step comprises the dehalogenation or desulfinylation of the compound of formula (IV) to produce compound of formula (V).

In an embodiment, step (c) is a halogenation, and step (d) comprises a dehalogenation step which can be performed in the presence of a base. The base can be selected from the group comprising imidazole, collidine, 2,6-lutidine, triethylamine, or 1,8-diazabicyclo[5.4.0]undec-7-ene (DBU). The dehalogenation reaction can be performed at a temperature between 30° C. and 130° C. Preferably, the dehalogenation reaction is performed in an aprotic solvent.

In another embodiment, step (c) is a sulfinylation, and step (d) comprises a desulfinylation which can be carried out with heat optionally in the presence of cupric sulfate. The temperature of the desulfinylation step can be between 80° C. and 130° C., preferably between 90° C. and 120° C., preferably between 100° C. and 115° C.

The next step in the process comprises the reduction of the compound of formula (V) with a reducing agent to produce compound of formula (I). Preferably, said reducing agent is a metal hydride compound. For example, the metal hydride compound can be selected from the group comprising $LiAlH_4$, $NaBH_4$, $NaBH(OAc)_3$, $ZnBH_4$, and $NaBH_4/CeCl_3$. preferably, said reducing agent is $NaBH_4/CeCl_3$.

For example said reduction can be performed in a suitable solvent or a mixture thereof, such as in tetrahydrofuran, or a mixture of methanol and tetrahydrofuran. The reaction can be performed at low temperatures such as below 15° C., for example below 10° C.

The present inventors have surprisingly found that the compound of formula (I) and its intermediates, could be obtained in good yield and improved purity.

The present process has the advantage that 3-$P^1$-oxyestra1,3,5(10),15-tetraen-17-ol of formula (I), and subsequently estetrol, can be obtained from estrone with improve yield compared to prior art processes, which is more convenient for an economical and industrial synthesis.

The present invention also encompasses a process for the preparation of estetrol, said process comprising preparing a compound of formula (I) using the process of the invention and further reacting compound of formula (I) to produce estetrol.

The present invention also encompasses the use of estetrol directly obtained by the process the invention for the manufacture of a pharmaceutical composition, preferably for use in a method selected from a method of hormone replacement therapy, a method of treating vaginal dryness, a method of contraception, a method of enhancing libido, of method of treating skin, a method of promoting wound healing, and a method of treating or preventing a disorder selected from the group consisting of autoimmune diseases, breast tumors and colorectal tumors.

The invention is illustrated but not limited by the following examples.

EXAMPLES

Example 1: Preparation of a Compound of Formula (I) wherein $P^1$ is tert-butyldimethylsilyl According to an Embodiment of the Invention

Step 1: 3-tert-butyldimethylsilyloxy-estra-1,3,5(10)-triene-17-one

To a solution of 3-hydroxy-estra-1,3,5(10)-triene-17-one (100 g, 0.370 mole) in 500 ml of dichloromethane was added tert-butyldimethylsilyl-chloride (58.3 g, 0.388 mole) and imidazole (26.4 g, 0.388 mole). The mixture was stirred for 24 hours at room temperature. Water (300 ml) was added and the organic layer was washed with 200 ml of water. After concentration the product was crystallized from a mixture of ethanol/diisopropyl ether, collected by filtration and dried. It weighted 145 g (95% yield).

$^1$HNMR (CDCl$_3$) δ 0.20 (s, 6H, (CH$_3$)$_2$—Si—), 0.90 (s, 3H, CH$_3$ at C-18), 1.00 (s, 9H, (CH$_3$)$_3$—C—Si—), 1.20-2.60 (m, 13H), 2.75-2.95 (m, 2H), 5.65-5.75 (m, 1H), 6.58 (broad s, 1H, H4), 6.63 (dd, 1H, H2), 7.12 (d, 1H, H1) mp: 171.6° C.

Step 2: 3-tert-butyldimethylsilyloxy-estra-1,3,5(10)-15-tetraene-17-one

A solution of potassium terbutylate (50 g, 0.45 mole) in 800 ml of tetrahydrofuran was treated with 3-tert-butyldimethylsilyloxy-estra-1,3,5(10)-triene-17-one (86.5 g, 0.225 mole) under nitrogen and stirred for 1 hour, then methyl benzenesulfinate (70.2 g, 0.45 mole) and triethylamine were added. After stirring for 2 hours the solution was poured in 1000 ml of water and 70 ml of hydrochloric acid keeping the temperature below 5° C. 1000 ml of toluene was added, phases are separated and the solution was heated to distill off the solvent until the temperature reached 115° C. Reflux was maintained for 5 hours.

Toluene was washed with two time water, and then partially concentrated. Heptane was added. After one hour at 5° C. the solid was collected by filtration and used in the reduction step without further purification.

$^1$HNMR (CDCl$_3$) δ 0.20 (s, 6H, (CH$_3$)$_2$—Si—), 1.00 (s, 9H, (CH$_3$)$_3$—C—Si—), 1.13 (s, 3H, CH$_3$ at C-18), 1.20-2.70 (m, 11H), 2.80-3.00 (m, 2H), 6.10 (dd, 1H, H15), 6.58 (broad s, 1H, H4), 6.62 (dd, 1H, H2), 7.11 (d, 1H, H1), 7.63 (dd, 1H, H16), mp: 165° C.

Step 3: 3-tert-butyldimethylsilyloxy-estra-1,3,5(10)-15-tetraene-17-ol

The material collected in step 2 was dissolved in THF 300 ml and a solution of cerium chloride heptahydrate (123 g, 0.33 mole) in methanol (300 ml) was added. The mixture was cooled to 0° C. and sodium borohybride (17.8 g, 0.47 mole, 1.5 q) was added portionwise keeping the temperature below 9° C. At this end of the addition the mixture was stirred for one hour then quenched by addition of a 2N HCl solution (100 ml), extracted with ethyl acetate and washed with water. The organic layer was partly evaporated then diisopropylether was added. The precipitate was collected by filtration and dried. After crystallization form a mixture of ethanol/diisopropyl ether the title compound was isolated in 90% yield as an off white solid.

$^1$HNMR (CDCl$_3$) δ 0.20 (s, 6H, (CH$_3$)$_2$—Si—), 0.89 (s, 3H, CH$_3$ at C-18), 1.00 (s, 9H, (CH$_3$)$_3$—C—Si—), 1.20-2.40 (m, 10H), 2.75-2.95 (m, 2H), 4.40 (broad s, 1H, H17), 5.65-5.75 (m, 1H), 5.95-6.10 (m, 1H), 6.57 (broad s, 1H, H4), 6.60 (dd, 1H, H2), 7.13 (d, 1H, H1) mp: 107.5° C.

Example 2: Preparation of a Compound of Formula (I) wherein P$^1$ is tert-butyldimethylsilyl According to an Embodiment of the Invention

Step 1: 3-tert-butyldimethylsilyloxy-estra-1,3,5(10)-triene-17-one 3-tert-butyldimethylsilyloxy-estra-1,3,5(10)-triene-17-one was prepared as described in step 1 of Example 1.

Step 2: 3-tert-butyldimethylsilyloxy-estra-1,3,5(10)-15-tetraene-17-one (via X═Br)

Copper(II) bromide (100 g, 0.45 mole) was added to a warm solution of 3-tert-butyldimethylsilyloxy-estra-1,3,5(10)-triene-17-one (86.4 g, 0.225 mole) in methanol (500 ml) and the mixture was heated under reflux for 2 hours. The hot mixture was filtered and was poured in a mixture of dichloromethane (1000 ml) and water (800 ml). The organic layer was washed with water.

To this solution imidazole (18.3 g, 0.27 mole) was added and heated under reflux for 6 hours. After cooling water (500 ml) was added and the organic layer was concentrated. The residue was crystallized from a mixture of ethyl acetate and heptane.

$^1$HNMR (CDCl$_3$) δ 0.20 (s, 6H, (CH$_3$)$_2$—Si—), 1.00 (s, 9H, (CH$_3$)$_3$—C—Si—), 1.13 (s, 3H, CH$_3$ at C-18), 1.20-2.70 (m, 11H), 2.80-3.00 (m, 2H), 6.10 (dd, 1H, H15), 6.58 (broad s, 1H, H4), 6.62 (dd, 1H, H2), 7.11 (d, 1H, H1), 7.63 (dd, 1H, H16), mp: 165° C.

Step 3: 3-tert-butyldimethylsilyloxy-estra-1,3,5(10)-15-tetraene-17-ol

The reduction step was performed as described in step 3 of example 1: The material collected in step 2 of example 2 was dissolved in THF and a solution of cerium chloride heptahydrate (about 1 eq) in methanol was added. The mixture was cooled to 0° C. and sodium borohybride (1.5 eq) was added portionwise keeping the temperature below 9° C. At this end of the addition the mixture was stirred for one hour then quenched by addition of a 2N HCl solution, extracted with ethyl acetate and washed with water. The organic layer was partly evaporated then diisopropylether was added. The precipitate was collected by filtration and dried. After crystallization form a mixture of ethanol/diisopropyl ether the title compound was isolated as an off white solid.

$^1$HNMR (CDCl$_3$) δ 0.20 (s, 6H, (CH$_3$)$_2$—Si—), 0.89 (s, 3H, CH$_3$ at C-18), 1.00 (s, 9H, (CH$_3$)$_3$—C—Si—), 1.20-2.40 (m, 10H), 2.75-2.95 (m, 2H), 4.40 (broad s, 1H, H17), 5.65-5.75 (m, 1H), 5.95-6.10 (m, 1H), 6.57 (broad s, 1H, H4), 6.60 (dd, 1H, H2), 7.13 (d, 1H, H1) mp: 107.5° C.

Example 3: Preparation of a Compound of Formula (I) wherein P$^1$ is tert-butyldimethylsilyl According to an Embodiment of the Invention

Step 1: 3-tert-butyldimethylsilyloxy-estra-1,3,5(10)-triene-17-one 3-tert-butyldimethylsilyloxy-estra-1,3,5(10)-triene-17-one was prepared as described in step 1 of Example 1.

Step 2: 3-tert-butyldimethylsilyloxy-estra-1,3,5(10)-15-tetraene-17-one (via X═pyridinesulfinic)

3-tert-butyldimethylsilyloxy-estra-1,3,5(10)-triene 17-one (8.64 g, 0.0225 mole) was added to a suspension of potassium hydride (3 eq. 35% dispersion in oil) in tetrahydrofuran 100 ml. methyl 2-pyridinesulfinate (5.3 g, 0.034 mole, 1.5 eq) was added. After 30 min at room temperature the reaction was poured into a sulfate buffer. The aqueous phase was neutralized by an aqueous solution of sodium carbonate then extracted with toluene. The solution was heated to 110° C. for one hour. After cooling to room temperature the solution was washed with a diluted solution of sodium hydroxide then with water. The organic layer was partly concentrated following by an addition of heptane. The 3-tert-butyldimethylsilyloxy-estra-1,3,5(10)-15-tetraene-17-one was collected by filtration.

$^1$HNMR (CDCl$_3$) δ 0.20 (s, 6H, (CH$_3$)$_2$—Si—), 1.00 (s, 9H, (CH$_3$)$_3$—C—Si—), 1.13 (s, 3H, CH$_3$ at C-18), 1.20-2.70 (m, 11H), 2.80-3.00 (m, 2H), 6.10 (dd, 1H, H15), 6.58 (broad s, 1H, H4), 6.62 (dd, 1H, H2), 7.11 (d, 1H, H1), 7.63 (dd, 1H, H16), mp: 165° C.

Step 3: 3-tert-butyldimethylsilyloxy-estra-1,3,5(10)-15-tetraene-17-ol

The reduction step was performed as described in step 3 of example 1: The material collected in step 2 of example 3 was dissolved in THF and a solution of cerium chloride heptahydrate in methanol was added. The mixture was cooled to 0° C. and sodium borohybride (1.5 eq) was added portionwise keeping the temperature below 9° C. At this end of the addition the mixture was stirred for one hour then quenched by addition of a 2N HCl solution, extracted with ethyl acetate and washed with water. The organic layer was partly evaporated then diisopropylether was added. The precipitate was collected by filtration and dried. After crystallization form a mixture of ethanol/diisopropyl ether the title compound was isolated as an off white solid.

$^1$HNMR (CDCl$_3$) δ 0.20 (s, 6H, (CH$_3$)$_2$—Si—), 0.89 (s, 3H, CH$_3$ at C-18), 1.00 (s, 9H, (CH$_3$)$_3$—C—Si—), 1.20-2.40 (m, 10H), 2.75-2.95 (m, 2H), 4.40 (broad s, 1H, H17), 5.65-5.75 (m, 1H), 5.95-6.10 (m, 1H), 6.57 (broad s, 1H, H4), 6.60 (dd, 1H, H2), 7.13 (d, 1H, H1) mp: 107.5° C.

It is to be understood that although preferred embodiments and/or materials have been discussed for providing embodiments according to the present invention, various modifications or changes may be made without departing from the scope and spirit of this invention.

The invention claimed is:

1. A process for the preparation of a compound of formula (I)

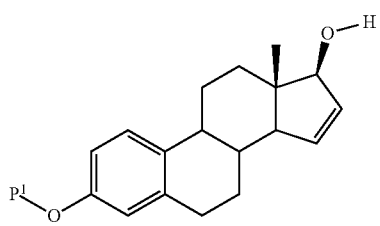

comprising the steps of
a) reacting a compound of formula (II) with a silylating agent to produce a compound of formula (III), wherein P$^1$ is R$^2$—Si—R$^3$R$^4$; R$^2$, R$^3$ and R$^4$ are each independently a group selected from C$_{1-6}$alkyl or phenyl, each group being optionally substituted by one or more substituents independently selected from fluoro or C$_{1-4}$alkyl;

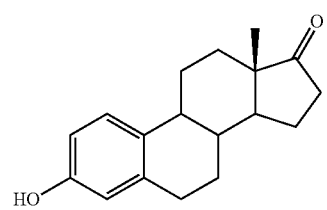

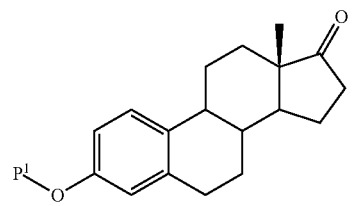

b) halogenation or sulfinylation of the compound of formula (III) to produce a compound of formula (IV); wherein X is halo, or —SO—R$^5$, and R$^5$ is a group selected from C$_{6-10}$aryl or heteroaryl, each group being optionally substituted by one or more substituents independently selected from chloro or C$_{1-4}$alkyl; wherein the halogenation or sulfinylation is performed by directly reacting the compound of formula (III) with a halogenation or sulfinylation reagent;

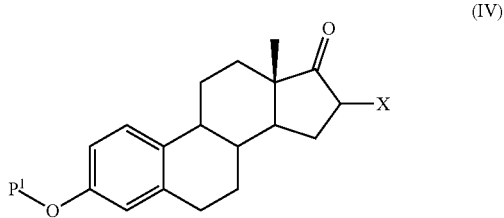

c) direct dehalogenation or desulfinylation of the compound of formula (IV) to produce compound of formula (V); and

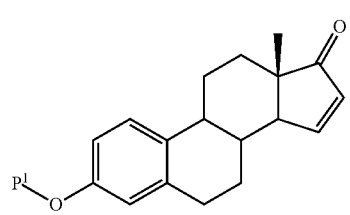

d) reacting the compound of formula (V) with a reducing agent to produce compound of formula (I).

2. The process according to claim 1, wherein step (b) is a sulfinylation and the sulfinylation is performed by reacting the compound of formula (III) with a base and with a sulfinylation reagent.

3. The process according to claim 1 wherein step (b) is a sulfinylation and a sulfinylation reagent is methyl 2-pyridinesulfinate, methyl benzenesulfinate, methyl 4-methylbenzenesulfinate, methyl 4-chloro-benzene sulfinate.

4. The process according to claim 2, wherein the base used in the sulfinylation step is selected from the group consisting of potassium hydride, potassium terbutylate, sodium hydride, sodium terbutylate and a mixture thereof.

5. The process according to claim 1, wherein step (b) is a halogenation and the halogenation is performed by reacting the compound of formula (III) with a halogenating reagent.

6. The process according to claim 1 wherein step (b) is a bromination and a brominating reagent is selected from the group consisting of copper(II) bromide, bromine, and pyridinium bromide perbromide.

7. The process according to claim 1, wherein the desulfinylation step is carried out with heat, or optionally in the presence of cupric sulfate.

8. The process according to claim 1, wherein the dehalogenation step is performed in the presence of a base.

9. The process according to claim 8, wherein the base is selected from the group consisting of imidazole, collidine, 2,6-lutidine, triethylamine, or 1,8-diazabicyclo[5.4.0]undec-7-ene.

10. The process according to claim 1, wherein step (d) is performed using a reducing agent selected from the group consisting of metal hydride compounds.

11. The process according to claim 1, wherein step (d) is performed using a reducing agent selected from the group consisting of NaBH$_4$/CeCl$_3$, LiAlH$_4$, NaBH$_4$, NaBH(OAc)$_3$, and ZnBH$_4$.

12. The process according to claim 1, wherein the silylating agent is selected from the group consisting of C$_{1-6}$alkylsilylchloride, C$_{1-6}$alkylsilyltriflate, phenylsilylchloride, phenylsilyltriflate, C$_{1-6}$alkylphenylsilylchloride, C$_{1-6}$alkylphenylsilyltriflate, each group being optionally substituted by one or more substituents independently selected from fluoro or $C_{1-4}$alkyl.

13. The process according to claim 1, wherein the acylating agent is selected from the group consisting of $C_{2-6}$alkenyl$C_{1-6}$alkanoates, $C_{2-6}$alkenyl$C_{3-6}$cycloalkanoates, acyl chlorides and anhydrides.

14. A process for the preparation of estetrol, said process comprising preparing a compound of formula (I) by a process,

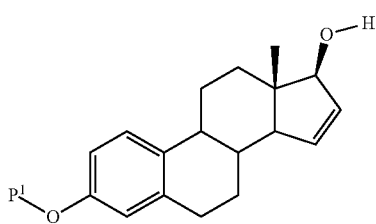
(I)

the process comprising the steps of:
a) reacting a compound of formula (II) with a silylating agent to produce a compound of formula (III), wherein $P^1$ is $R^2$—Si—$R^3R^4$; $R^2$, $R^3$ and $R^4$ are each independently a group selected from $C_{1-6}$alkyl or phenyl, each group being optionally substituted by one or more substituents independently selected from fluoro or $C_{1-4}$alkyl;

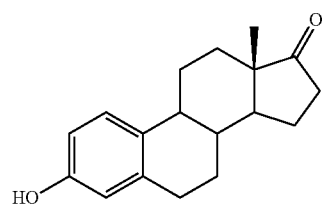
(II)

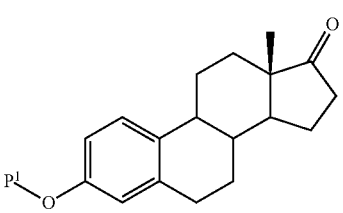
(III)

b) halogenation or sulfinylation of the compound of formula (III) to produce a compound of formula (IV); wherein X is halo, or —SO—$R^5$, and $R^5$ is a group selected from $C_{6-10}$aryl or heteroaryl, each group being optionally substituted by one or more substituents independently selected from chloro or $C_{1-4}$alkyl;

wherein the halogenation or sulfinylation is performed by directly reacting the compound of formula (III) with an halogenation or sulfinylation reagent;

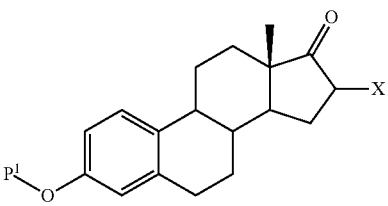
(IV)

c) direct dehalogenation or desulfinylation of the compound of formula (IV) to produce compound of formula (V); and

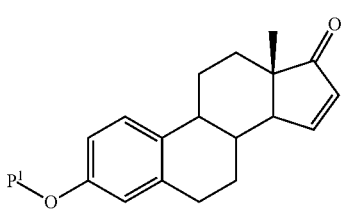
(V)

d) reacting the compound of formula (V) with a reducing agent to produce compound of formula (I);
and further reacting compound of formula (I) to produce estetrol.

15. The process according to claim 14, wherein step (b) is a sulfinylation and the sulfinylation is performed by reacting the compound of formula (III) with a base and with a sulfinylation reagent.

16. The process according to claim 14 wherein step (b) is a sulfinylation and a sulfinylation reagent is methyl 2-pyridinesulfinate, methyl benzenesulfinate, 4-methyl-benzenesulfinate, methyl 4-chloro-benzene sulfinate.

17. The process according to claim 15, wherein the base used in the sulfinylation step is selected from the group consisting of potassium hydride, potassium terbutylate, sodium hydride, sodium terbutylate and a mixture thereof.

18. The process according to claim 14, wherein step (b) is a halogenation and the halogenation is performed by reacting the compound of formula (III) with a halogenating reagent.

19. The process according to claim 14 wherein step (b) is a bromination and a brominating reagent is selected from the group consisting of copper(II) bromide, bromine, and pyridinium bromide perbromide.

* * * * *